(12) United States Patent
Kernot (10) Patent No.: US 7,841,350 B2
(45) Date of Patent: Nov. 30, 2010

(54) CREDIT CARD TYPE DISPENSER FOR FILAMENTARY MATERIALS

(76) Inventor: Christopher Joseph Kernot, P O Box 5025, Port Vila (VU)

( * ) Notice: Subject to any disclaimer, the term of this patent is extended or adjusted under 35 U.S.C. 154(b) by 1314 days.

(21) Appl. No.: 10/552,739

(22) PCT Filed: Apr. 23, 2004

(86) PCT No.: PCT/NZ2004/000079

§ 371 (c)(1), (2), (4) Date: Oct. 12, 2005

(87) PCT Pub. No.: WO2004/093717

PCT Pub. Date: Nov. 4, 2004

(65) Prior Publication Data

US 2006/0283479 A1 Dec. 21, 2006

(30) Foreign Application Priority Data

Apr. 23, 2003 (NZ) .................................. 525470

(51) Int. Cl.
*A61C 15/00* (2006.01)
(52) U.S. Cl. .................... 132/325; 132/324; 132/323
(58) Field of Classification Search ......... 132/321–329; 206/234, 63.5
See application file for complete search history.

(56) References Cited

U.S. PATENT DOCUMENTS

| | | | |
|---|---|---|---|
| 2,692,698 A * | 10/1954 | Waterman | .................... 220/350 |
| 3,480,190 A | 11/1969 | Freedman | |
| 3,525,462 A | 8/1970 | Freedman | |
| 4,084,692 A | 4/1978 | Bilweis | ....................... 206/403 |
| 4,162,688 A * | 7/1979 | Tarrson et al. | ............... 132/322 |
| 4,327,755 A | 5/1982 | Endelson | ....................... 132/92 |
| 4,881,560 A | 11/1989 | Blank et al. | ................. 132/324 |
| 4,925,073 A | 5/1990 | Tarrson et al. | ................. 225/44 |
| 5,076,423 A | 12/1991 | Russack | .................... 206/63.5 |
| D326,339 S * | 5/1992 | Sherman et al. | ............... D28/66 |
| 5,156,311 A | 10/1992 | Spencer, Jr. | ................... 225/41 |
| 5,199,452 A * | 4/1993 | Cheng | ......................... 132/325 |
| 5,201,330 A * | 4/1993 | Won | ........................... 132/325 |
| 5,649,659 A | 7/1997 | Saunders | ....................... 225/39 |
| 5,678,578 A * | 10/1997 | Kossak et al. | ............... 132/322 |
| 5,678,580 A | 10/1997 | Sherman | ..................... 132/324 |
| 5,722,439 A | 3/1998 | Endelson | .................... 132/321 |
| 5,787,907 A | 8/1998 | Endelson | .................... 132/321 |

(Continued)

FOREIGN PATENT DOCUMENTS

| | | |
|---|---|---|
| EP | 0666224 A1 | 8/1995 |
| JP | 07315697 A | 12/1995 |
| WO | WO01/15621 | 8/2001 |

*Primary Examiner*—Robyn Doan
(74) *Attorney, Agent, or Firm*—Jacobson Holman PLLC (57) ABSTRACT

A credit card type dental floss dispenser for carrying in a wallet or the like. The dispenser comprises a substantially closed housing (57) having oppositely disposed substantially planar wall portions, narrowly spaced apart and a supply of dental floss within. The floss dispenser includes a dispensing area (56) for dispensing the floss including a cutter (64) for severing the floss into desired lengths. The dispensing area is enclosed by a moveable cover (58) in order to improve hygiene and prevent dirt from contamination the floss supply. A floss storage reel may be visible through the housing and may include advertising or other indicia. The dispenser may also include means to prevent rotation of the reel in one direction.

21 Claims, 8 Drawing Sheets

U.S. PATENT DOCUMENTS

| | | | |
|---|---|---|---|
| 5,806,666 A | 9/1998 | Chiang et al. | 206/63.5 |
| 6,295,996 B1 | 10/2001 | Dickie | 132/321 |
| 6,295,997 B1 | 10/2001 | Dickie | 132/321 |
| 6,302,121 B1 | 10/2001 | McConnell | 132/321 |
| D485,945 S * | 1/2004 | Blasi et al. | D28/66 |
| 6,694,667 B2 * | 2/2004 | Davis | 43/54.1 |

* cited by examiner

CREDIT CARD TYPE DISPENSER FOR FILAMENTARY MATERIALS

This is a nationalization of PCT/NZ04/000079 filed Apr. 23, 2004 and published in English.

BACKGROUND TO THE INVENTION

1. Field of the Invention

This invention relates to a compact dispenser for dispensing a filamentary material, for example dental floss or dental floss tape.

2. Summary of the Prior Art

It is well established that the accumulation of plaque on the teeth and gums is a significant contributing factor to dental disease. The therapeutic value of flossing in order to dislodge plaque and food debris collected between the teeth is well known and the dental profession generally agrees that regular flossing promotes dental health.

Despite the well established advantages of flossing, many busy people may find it difficult to find the time to floss their teeth in their daily routine. Many people therefore prefer to floss their teeth while away from home. However, carrying dental floss may be inconvenient especially when the dental floss dispenser is bulky or inconveniently shaped.

Credit card type dental floss dispensers are known in the art. Credit cards are in widespread use and therefore most wallets, purses and the like provide for storage of credit cards. It is therefore convenient to have a dental floss dispenser substantially the same size and/or shape as a credit card so that it can be conveniently carried in a wallet, purse or credit card holder or the like.

Examples of credit card type dental floss dispensers known in the art are U.S. Pat. No. 4,327,755, U.S. Pat. No. 5,649,659, U.S. Pat. No. 4,881,560 and U.S. Pat. No. 5,076,423. However, a disadvantage of these designs arises from the dental floss cutter and the end portion of the dental floss, being exposed in the environment when stored. This gives rise to the possibility of poor hygiene. Further, the dental floss may become snagged while at the bottom of a purse or in a wallet. When the dental floss dispenser is taken out, the snagged dental floss may cause unwanted withdrawal of the dental floss from the dispenser. Further disadvantages of the prior art may arise from the credit card type dental floss dispenser being too flimsy and therefore prone to warping or breaking.

A further disadvantage may arise from the cutter of the dispenser being exposed to the environment, which gives rise to the potential for damage of other articles such as the wallet or pocket if they come into contact with the sharp cutter.

DEFINITION

The word "floss" is used throughout the specification to describe the material which is dispensed from the dispenser of the current invention. It is to be understood that "floss" is used for convenience only and is to include many types of filamentary material such as: dental tape, dental floss, cord, twine, surgical sutures, cotton, and small gage wire.

SUMMARY OF THE INVENTION

It is an object of the present invention to provide a filament material dispenser which goes some way to overcoming the above disadvantages or at least provides the public with a useful choice.

In a first aspect the present invention may be broadly said to consist in a dispenser comprising:

a substantially closed housing having a pair of oppositely disposed substantially planar wall portion, substantially parallel and spaced apart by less than 6 mm, and a dispensing area, a supply of filamentary material within said housing, a moveable cover connected with said housing to be moveable between a first operating condition, and a second operating condition, wherein said cover when in said first operating condition encloses said dispensing area, and said cover when in said second operating condition exposes said dispensing area.

Preferably said housing includes a dispensing aperture, opening into said dispensing area and within said dispensing area, a cutter for severing said filamentary material exiting said housing through said aperture.

Preferably said housing has a general shape defined by a boundary and said dispensing area is recessed into said housing to lie wholly within said boundary of said general shape.

Preferably said cover in said first operating condition, lies substantially within said boundary.

Preferably said cover is slidable between said first operating condition and said second operating condition in a sliding direction, and said sliding direction is substantially parallel to said wall portions.

Preferably said cover is biased toward its said first operating condition.

Alternatively said cover is pivotally moveable between said first and said second operating conditions, and the axis of said pivotal motion is substantially perpendicular to said wall portions.

Alternatively said cover is hinged to a said wall portion, and said cover hinging about an axis parallel to said wall portion.

Preferably said supply of filamentary material is a rotatably supported reel.

Preferably said supply is a reel, and at least one said wall portion includes a circular aperture, said circular aperture receiving a bearing portion of said reel such that said reel is rotatably supported between said wall portions with said bearing portions projecting into said aperture.

Preferably said reel includes indicia on an outer surface, and said outer surface is visible through said circular aperture.

Preferably said dispenser further comprising:

a rotation limiting means for preventing rotation of said reel in a wind-up direction, said limiting means comprising a ratchet track having a series of teeth with ramped leading surfaces alternating with radial or undercut trailing surfaces on one of said reel or said wall, and at least one complimentary shaped ratchet tooth on the other of said reel or said wall, one of said ratchet tooth, or said track teeth being movable, said track teeth and said at least one ratchet tooth arranged in a meshing relationship and allowing rotation of said reel in an unwinding direction, by movement of one of said movable ratchet tooth or said movable track teeth, to ride over said other of said ratchet tooth or said track teeth.

Preferably said dispenser further comprising an incomplete ring spacer member located between spaced side walls of said reel, said ring having a diameter approximately the same as said reel, and said ring having a thickness approximately the same as said space between said side walls, said ring including indexing means, and at least one of said walls including correspondingly shaped indexing means, said indexing means engaging to prevent rotation of said ring, wherein said filamentary material passes through a gap in said incomplete ring.

Preferably said wall portions include step portions adapted to lap one another and substantially seal around a perimeter of said wall portions.

Preferably said wall portions are connected together by a living hinge.

Preferably said wall portion includes a further aperture adapted to receive an attachment means.

Preferably said cover includes one or more surface features to improve grip.

Preferably said housing includes at least one guide to direct said filamentary material from said supply to said dispensing area, and said guide including a plurality of barbs to impede travel of filamentary material through said guide in one direction.

Preferably said wall portions are fastened together by a reversible fastening means for example, cooperating snap lock fasteners.

In a further aspect the present invention may be broadly said to consist in a dispenser comprising:

a substantially closed housing having a pair of oppositely disposed substantially planar wall portions, substantially parallel and spaced apart by less than 6 mm, and a dispensing area a supply of filamentary material within said housing, wherein said supply is a reel, and at least one said wall portion includes a circular aperture, said circular aperture receiving a bearing portion of said reel such that said reel is rotatably supported between said wall portions with said bearing portions projecting into said aperture.

Preferably said reel includes indicia on an outer surface, and said outer surface is visible through said circular aperture.

Preferably said wall portions include step portions adapted to lap one another and substantially seal around a perimeter of said wall portions.

Preferably said wall portions are connected together by a living hinge.

Preferably said wall portion includes a further aperture adapted to receive an attachment means.

Preferably said cover includes one or more surface features to improve grip.

Preferably said housing includes at least one guide to direct said filamentary material from said supply to said dispensing area, and said guide including a plurality of barbs to impede travel of filamentary material through said guide in one direction.

Preferably said wall portions are fastened together by a reversible fastening means for example, cooperating snap lock fasteners.

In a further aspect the present invention may be broadly said to consist in a dispenser comprising:

a substantially closed housing having a pair of oppositely disposed substantially planar wall portions, substantially parallel and spaced apart by less than 6 mm, and a dispensing area a supply of filamentary material within said housing, said supply of filamentary material being a reel rotatably supported within said housing, a rotation limiting means for preventing rotation of said reel in a wind-up direction, said limiting means comprising a ratchet track having a series of teeth with ramped leading surfaces alternating with radial or undercut trailing surfaces on one of said reel or said wall, and at least one complimentary shaped ratchet tooth on the other of said reel or said wall, one of said ratchet tooth, or said track teeth being movable, said track teeth and said at least one ratchet tooth arranged in a meshing relationship and allowing rotation of said reel in an unwinding direction, by movement of one of said movable ratchet tooth or said movable track teeth, to ride over said other of said ratchet tooth or said track teeth.

Preferably said dispenser further comprising an incomplete ring spacer member located between spaced side walls of said reel, said ring having a diameter approximately the same as said reel, and said ring having a thickness approximately the same as said space between said side walls, said ring including indexing means, and at least one of said walls including correspondingly shaped indexing means, said indexing means engaging to prevent rotation of said ring, wherein said filamentary material passes through a gap in said incomplete ring.

Preferably said wall portions include step portions adapted to lap one another and substantially seal around a perimeter of said wall portions.

Preferably said wall portions are connected together by a living hinge.

Preferably said wall portion includes a further aperture adapted to receive an attachment means.

Preferably said cover includes one or more surface features to improve grip.

Preferably said housing includes at least one guide to direct said filamentary material from said supply to said dispensing area, and said guide including a plurality of barbs to impede travel of filamentary material through said guide in one direction.

Preferably said wall portions are fastened together by a reversible fastening means for example, cooperating snap lock fasteners.

In a further aspect the present invention may be broadly said to consist in a dispenser comprising:

a substantially closed housing having a pair of oppositely disposed substantially planar wall portion, substantially parallel and spaced apart by less than 6 mm, and a dispensing area, a supply of filamentary material within said housing, wherein said supply is a reel, and at least one said wall portion includes a circular aperture, said circular aperture receiving a bearing portion of said reel such that said reel is rotatably supported between said wall portions with said bearing portions projecting into said aperture, wherein said dispenser further comprises, a rotation limiting means for preventing rotation of said reel in a wind-up direction, said limiting means comprising a ratchet track having a series of teeth with ramped leading surfaces alternating with radial or undercut trailing surfaces on one of said reel or said wall, and at least one complimentary shaped ratchet tooth on the other of said reel or said wall, one of said ratchet tooth, or said track teeth being movable, said track teeth and said at least one ratchet tooth arranged in a meshing relationship and allowing rotation of said reel in an unwinding direction, by movement of one of said movable ratchet tooth or said movable track teeth, to ride over said other of said ratchet tooth or said track teeth.

Preferably said reel includes indicia on an outer surface, and said outer surface is visible through said circular aperture.

Preferably said dispenser further comprising an incomplete ring spacer member located between spaced side walls of said reel, said ring having a diameter approximately the same as said reel, and said ring having a thickness approximately the same as said space between said side walls, said ring including indexing means, and at least one of said walls including correspondingly shaped indexing means, said indexing means engaging to prevent rotation of said ring, wherein said filamentary material passes through a gap in said incomplete ring.

In a further aspect the present invention may be broadly said to consist in a dispenser comprising:

a substantially closed housing having a pair of oppositely disposed substantially planar wall portion, substantially parallel and spaced apart by less than 6 mm, and a dispensing area, a supply of filamentary material within said housing, wherein said supply is a reel, a moveable cover connected with said housing to be moveable between a first operating condition, and a second operating condition, wherein said cover when in said first operating condition encloses said dispensing area, and said cover when in said second operating condition exposes said dispensing area, wherein said dispenser further comprises a rotation limiting means for preventing rotation of said reel in a wind-up direction, said limiting means comprising a ratchet track having a series of teeth with ramped leading surfaces alternating with radial or undercut trailing surfaces on one of said reel or said wall, and at least one complimentary shaped ratchet tooth on the other of said reel or said wall, one of said ratchet tooth, or said track teeth being movable, said track teeth and said at least one ratchet tooth arranged in a meshing relationship and allowing rotation of said reel in an unwinding direction, by movement of one of said movable ratchet tooth or said movable track teeth, to ride over said other of said ratchet tooth or said track teeth.

Preferably said dispenser further comprising an incomplete ring spacer member located between spaced side walls of said reel, said ring having a diameter approximately the same as said reel, and said ring having a thickness approximately the same as said space between said side walls, said ring including indexing means, and at least one of said walls including correspondingly shaped indexing means, said indexing means engaging to prevent rotation of said ring, wherein said filamentary material passes through a gap in said incomplete ring.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

As a matter of convenience, the present invention is described in terms of a dental floss dispenser. However, the dispenser of the present invention is to be understood as suitable for dispensing many types of filamentary material and it is not limited in application to dental floss. With reference to FIGS. 1 to 5 a first preferred embodiment of the present invention will now be described.

Figure 1:
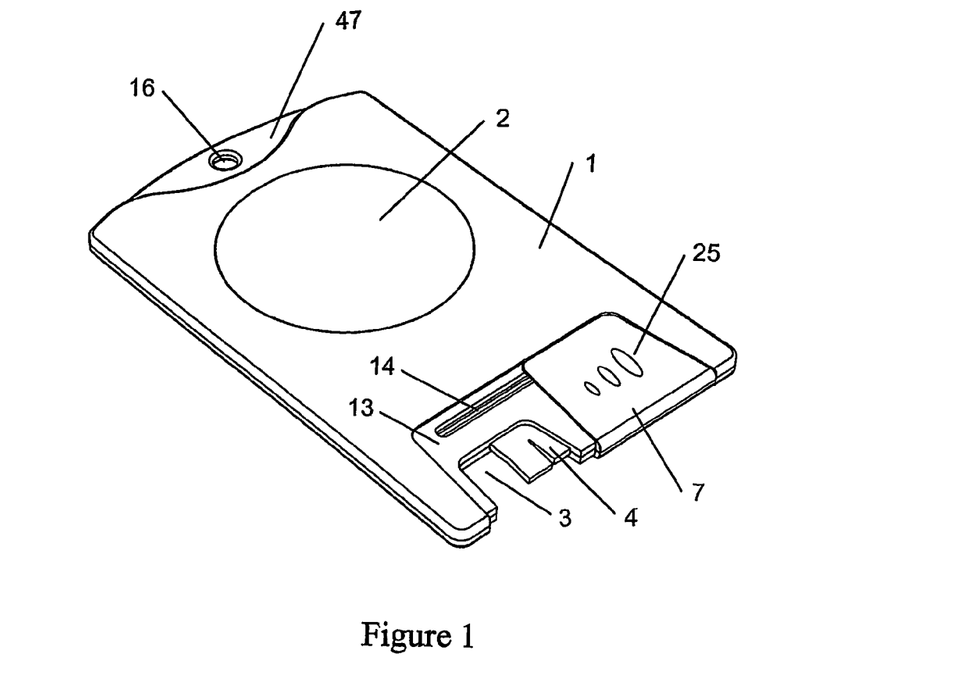
FIG. 1 is a perspective view of a floss dispenser according to a first preferred embodiment of the present invention.
Figure 2:
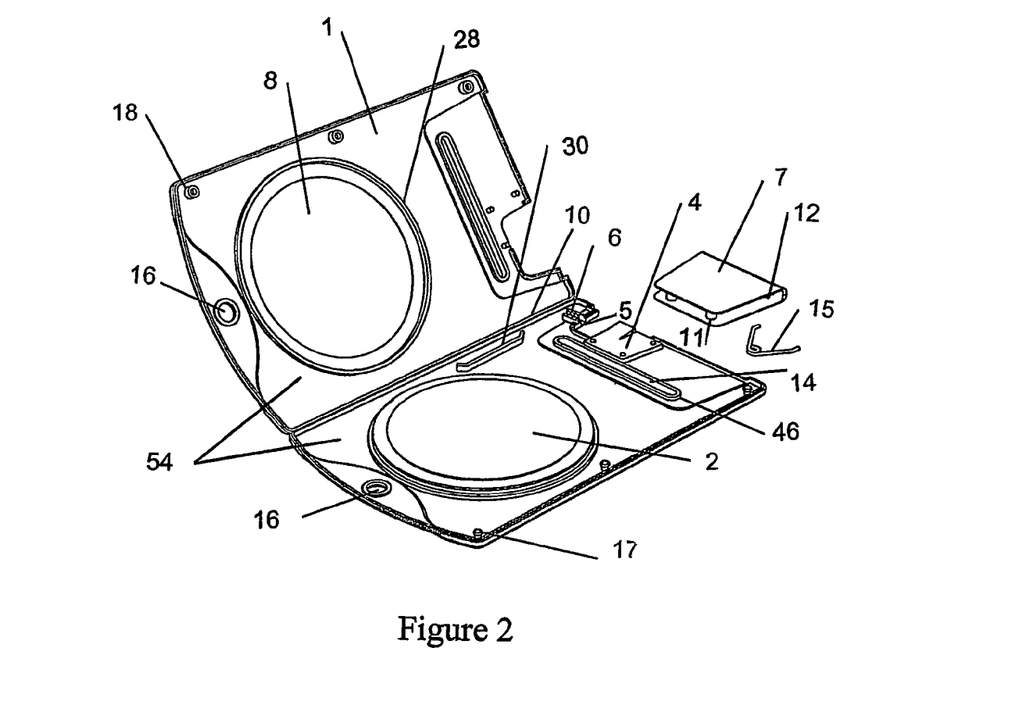
FIG. 2 is a partially exploded view of the dental floss dispenser shown in FIG. 1.

Housing 1 is substantially closed by lip portions around its periphery, and contains reel 2, on which dental floss is wound. The reel is rotatably supported within the housing such that the reel can rotate to unwind dental floss as it is withdrawn from the housing. The housing includes a dispensing area 3 which includes an aperture 5 through which the dental floss exits the housing, and a cutter 4, which can be used to sever the dental floss at the required length before use. A cover member 7 is provided to enclose the dispensing area when not in use, in order to provide increased hygiene.

The housing member 1 consists of two planar wall portions 54, which form two co-operating halves joined along an edge via a living hinge 10. When the housing is assembled as shown in FIG. 1, the wall portions are oppositely disposed and the housing is approximately the size and shape of a credit card. The wall portions 54 are narrowly spaced so that the thickness of the dispenser is less than approximately 6 mm. In practice, it is likely that the overall thickness of the dispenser will not be significantly less than approximately 2 mm. Each half of housing 1 has a circular cut-out aperture 8, which is adapted to receive corresponding raised lip 9, of reel 2. The interaction between the housing halves and the reel enable the reel to effectively become part of the housing in order to achieve a reduced dispenser thickness without significantly altering the flexural rigidity of the dispenser. Increased capacity and stiffness is important for thin credit card type dispensers. A dispensing area 3 is recessed in housing 1 so that the dispensing area lies within the general boundary shape of the rectangular dispenser. The dispensing area is indented within the perimeter of the housing, and is also recessed within the thickness of the housing to lie within the general boundary shape. A cutter 4 is provided in the dispensing area 3 and is adapted to receive and cut dental floss emerging from housing 1 through dispensing aperture 5.

Figure 3:
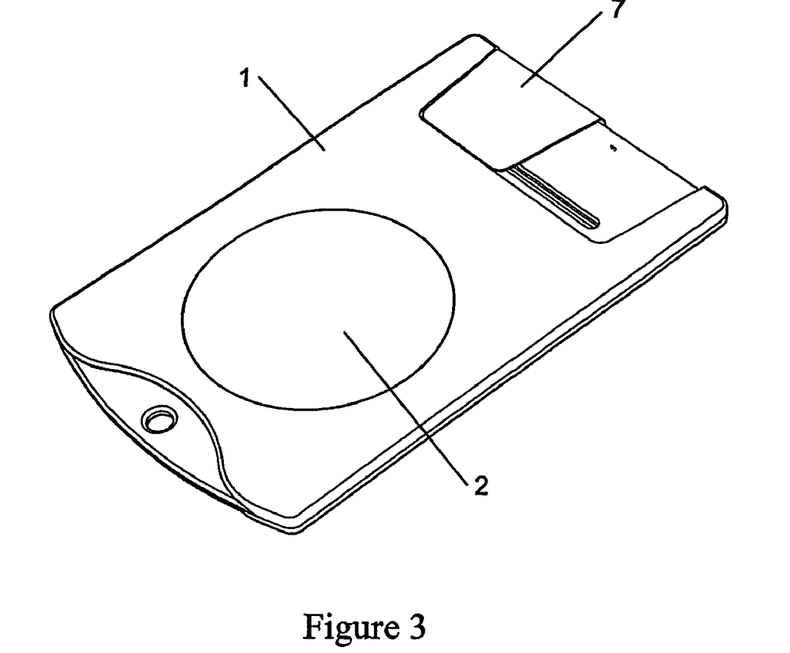
FIG. 3 is a perspective view of the dental floss dispenser of FIG. 1, shown with the cover closed.

A movable sliding cover 7 is provided having two operating conditions. In a first operating condition, sliding cover 7 is positioned such that it substantially encloses the dispensing area 3, which includes the cutter 4, and the dispensing aperture 5 as shown in FIG. 3. The cover 7 is shaped to snugly fit and slide within the recessed portion 13 of the dispensing area 3. The recessed portion 13 also provides an overlapping fit between the cover 7 and the housing 1 in order to prevent entry of unwanted dirt and debris into the dispensing area when the cover is in its first (closed) operating position. The recess 13 also preferably allows the outside dimensions of the sliding cover to substantially fit within the thickness of the closed housing. When retracted in a sliding direction, the sliding cover 7 takes up its second operating position which exposes dispensing area 3, including cutter 4 and dispensing aperture 5, so that the user can dispense and cut a portion of dental floss as required. In this embodiment, the movement directions of the cover are substantially parallel to the planner wall portions 54. The cover is shown in its second (open) position in FIG. 1.

A groove 14 is provided in housing 1 and runs substantially parallel to the sliding direction of the cover 7. Cover 7 may be provided with one or more protrusions 11, adapted to co-operate with groove 14 of the housing 1. When the dispenser is fully assembled for use, the protrusions 11 extend through, and interlock with, groove 14 to enable sliding of cover 7 between its first and second operating position while also preventing removal of the cover 7 from engagement with the housing 1. Groove 14 preferably extends completely through the housing although it is anticipated that groove 14 need not extend entirely through the housing. The groove 14 in housing 1 is preferably configured such that it does not open into the interior compartment of the housing where the dental floss reel is situated. For this purpose inward protruding lips 46 are provided around the perimeter of groove 14. When the two halves of the housing 1 are closed, the inward protruding lips mate and partition groove 14 from the inner portion of the housing where the reel is situated.

When not in use, it is preferable that cover 7 remains in its first, closed operating position, preventing contamination of the dispensing area and the dental floss. In order to achieve this, a biasing means such as spring 15 may be provided. Spring 15 is configured such that it interacts between the housing 1 and a spring tab 12 located on cover 7. A protrusion may also be provided on housing 1 in order to locate spring 15. Further protrusions may also be provided for spring 15 to bear against, such that the spring biases cover 7 toward its first operating (closed) position. Alternatively, instead of a torsion spring, other biasing means may be suitable such as: flat springs, integral plastic, cantilevered spring, or rubber band. It is also envisaged that it may be advantageous to hold the cover open against the biasing means when the cover is fully retracted, in order to provide improved access to the dental floss. An indexing protrusion and corresponding recess may be utilised for this purpose.

The housing 1 may also be provided with an aperture 16 on an attachment portion 47, which is suitable for use as an attachment means to a key ring or the like. In a similar manner to groove 14, aperture 16 is preferably configured such that the co-operating halves of housing 1, form aperture 16, through the housing without exposing the inner cavity containing reel 2, to the outside environment. Alternatively, an aperture may be provided in only one half of the housing, while the other half is indented to allow access to the attachment aperture.

Figure 4:
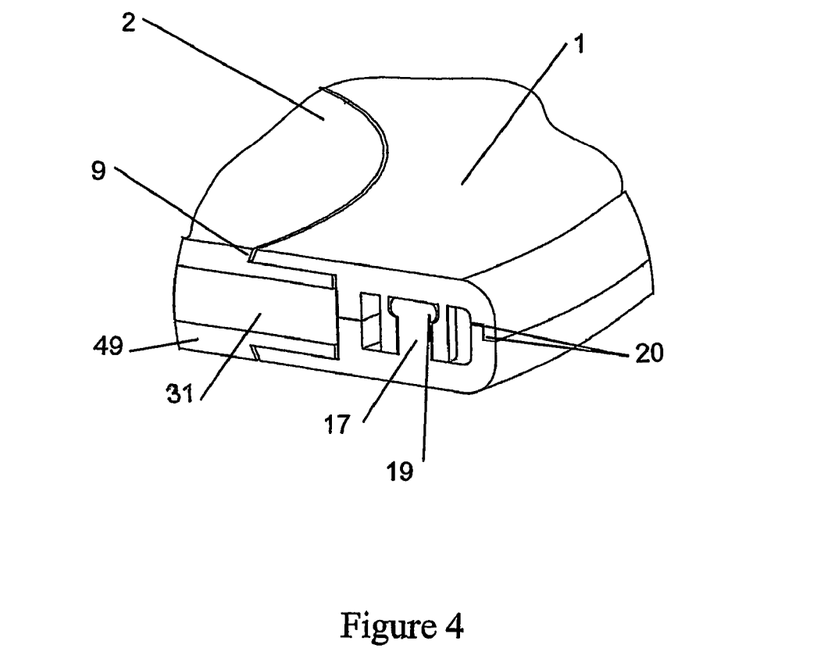
FIG. 4 is a cutaway view of a dental floss dispenser housing and reel showing the interaction between the negative detail of the reel and the housing.

In order to hold the two housing halves together in a substantially sealed manner after assembly, a plurality of cooperating fastening means 17, 18 may be provided. For this purpose male fastening protrusions 17 are provided on one half of housing 1, and female fastening means 18 are provided in complimentary positions on the other half of housing 1. In use the housing is assembled and snapped closed such that the male protrusions 17 engage tightly with the female fastening means 18. With reference to FIG. 4, the male fastening means 17 may also be provided with a bump off portion 19 to ensure proper fastening between the male and female complimentary fastening means. This type of non-permanent fastening means gives rise to the advantage that the housing may be opened for the purpose of replacing the dental floss reel as desired, and ease of assembly.

With reference to FIG. 4, complimentary stepped edges 20 along the perimeter of each half of housing 1 are preferably provided. The complimentary stepped edges 20, provide additional inter-engagement between the respective housing halves in order to increase the structural integrity of the assembled housing. The inter-engagement helps prevent distortion of the housing due to bending and twisting. Lapping of the joints between respective walls of the housing also helps seal the housing against contamination. The complimentary edges may also be thicker than the wall portions of the housing 1, in order to further enhance the engagement and sealing the housing members. For the same purpose it is also envisaged that the edges may include further features such as tongue and groove type joints.

Figure 5:
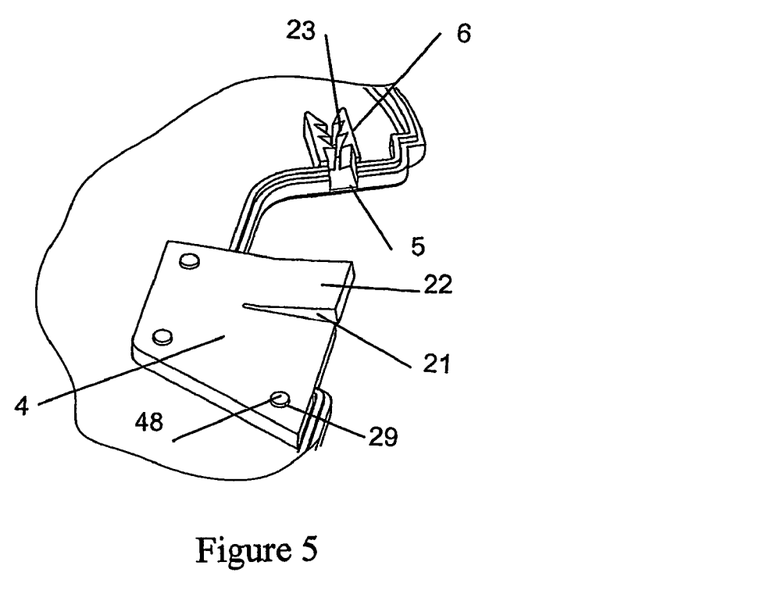
FIG. 5 is a cutaway view of a dental floss dispenser showing detail of the barbed floss guide, and cutter.

The cutter 4 is located and fixed in the dispensing area 3, via a suitable fastening means, to the housing 1. With reference to FIG. 5, cutter 4 may be provided with a plurality of apertures 29 which are adapted to receive a plurality of protrusions 48 integral with housing 1. The tips of the protrusions 48 may be swaged or melted such that the cutter 4 is firmly located and fixed to the housing. Alternatively, suitable fastening means for fixing cutter 4 may include: adhesive fastening, fixing via screws or an interference fit between the cutter plate 4, and features of the housing. A cutting groove 21 is located in the cutter plate 4 which in use is capable of severing the dental floss. A splayed tip portion 22 of cutter 4, preferably extends away from the plane of the cutter plate 4, in order to provide for improved access of the dental floss to the cutting groove 21. The splayed tip may extend in either direction away from the plane of the cutter to potentially better accommodate left-handed or right handed operation. It is also envisaged that the splayed tip portion of the cutter 4 may extend away from the main body of the cutter, in the plane of the cutter plate. In such a case the overall thickness of the dispenser is potentially reduced. The cutter may also serve to hold the floss in position after cutting, in order to aid gripping of the end of the floss when a user wishes to withdraw and cut some floss. Cutting groove 21 may also be provided with sharpened edges in order to aid severing of the dental floss. Preferably the cutter is adapted to grip the unsevered portion of the dental floss after cutting in order to prevent the loose end from moving about the dispensing area.

A floss guide 6 may also be provided to guide the dental floss as it is withdrawn towards the dispensing aperture 5. The inner surfaces of the floss guide channel 6 may also include a plurality of protrusions or barbs 23, which in use, help prevent retraction of the dental floss into the housing, thus making it difficult for a user to retrieve. In use the floss guide also acts to ensure that dental floss is withdrawn smoothly from the reel and does not become snagged on any internal features of the housing. Further guides 30 may also be provided along the path of the dental floss in order to ensure trouble free passage of the dental floss, from the reel, through the housing, and out of the dispensing aperture, as shown in FIG. 2.

With reference to FIGS. 1-4, the dental floss reel 2 is preferably circular in cross section with an internal annular space or groove 31, for receiving the dental floss winds. The sidewalls 49 of the dental floss reel 2 include raised lips 9, of substantially the same size and shape of the circular cut-out aperture 8 in housing 1. In use, the raised lips 9 at least partially protrude into the corresponding circular cut-outs on each half of the housing. The raised lips 9 interact with cut-out 8 to provide bearing surfaces for rotatably mounting and centering the reel within the housing. The bearing surfaces may be perpendicular to the plane of the housing, or on an angle, or may also include tongue-in-groove type features to improve sealing. The interaction between the raised lips and the cut-outs also provides additional structural strength to the floss dispenser. The clearance between raised lips 9 and cut-outs 8, is preferably small in order to increase the hygiene of the dispenser by creating a tortuous path which debris must follow to enter the inner cavity formed by the walls of the housing in which the dental floss reel 2 resides. With reference to FIG. 2 additional features such as a raised annular shielding protrusion 28 may also be provided in the housing in order to further shield the dental floss reel from potential contamination. An aperture through the complementary shielding wall portions in the housing is provided to allow the passage of dental floss from the reel to the dispensing area.

One or both sides of the reel 2, may be provided with graphics or advertising indicia as required. In use, as the dental floss is withdrawn from the dispenser the reel 1 rotates, and with it the graphic also rotates, which may give rise to an advantageous aesthetic appeal.

It will be appreciated that there are a number of possible alternatives and variations of the present invention that offer additional options or advantages. The preferred embodiments described and illustrated throughout this specification disclose some of these envisaged variations. Each preferred embodiment may illustrate one or more specific variations. The particular combination of features and variations presented in each of the embodiments described is not intended to be limiting in any sense. It is intended only that the variations be presented and described as representative samples of the many possible advantageous combinations of features which can be applied to a dispenser according to the present invention. It will also be appreciated that the following embodiments include features of the first embodiment which are not described again in detail.

Figure 6:
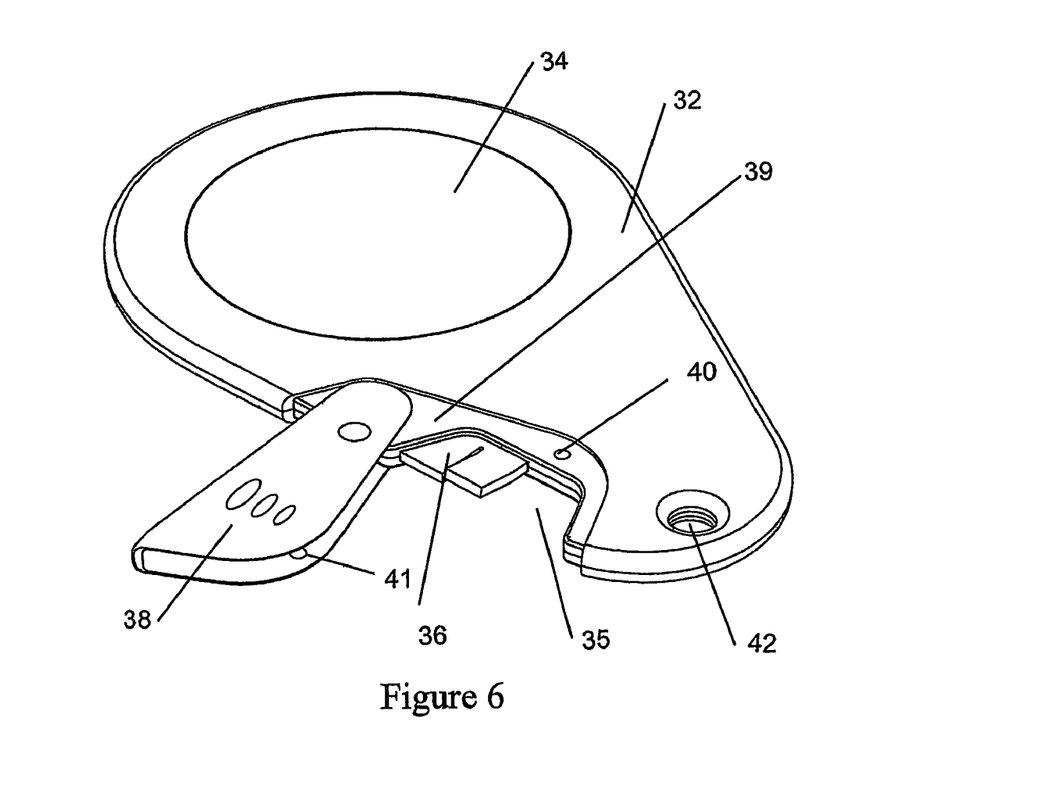
FIG. 6 is a perspective view of a further embodiment of the present invention having a pivoting cover.
Figure 7:
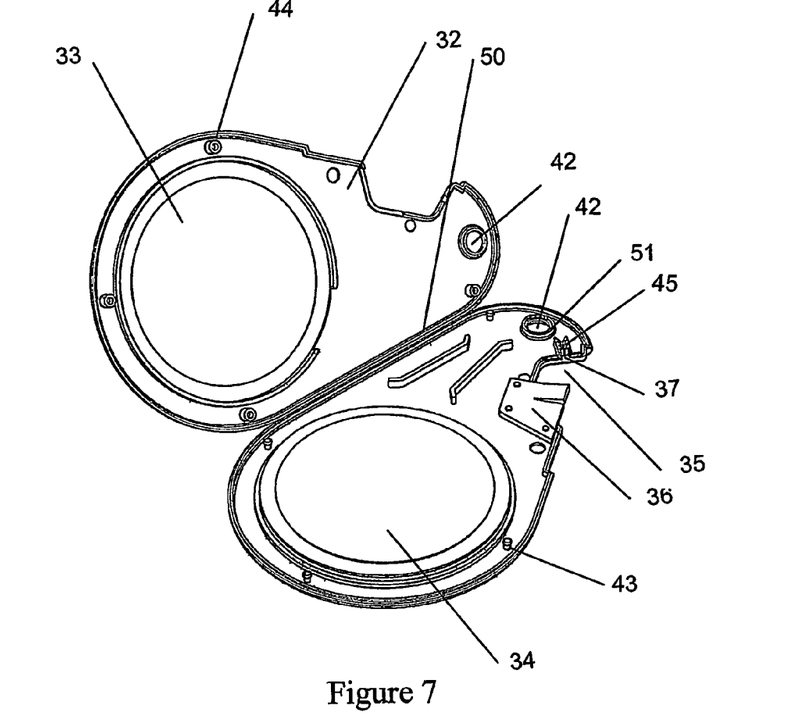
FIG. 7 is an inside view of the dental floss dispenser housing pictured in FIG. 6.

With reference to FIGS. 6 and 7 a second preferred embodiment of the present invention, including some additional or alternative features will now be described.

Housing 32 is constructed from two generally planar co-operating walls which are joined along an edge via a living hinge 50. The two halves of the housing, when fully assembled form a dispenser housing 32 approximately the size of a credit card in order to allow the dispenser to fit within a credit card pouch or wallet or the like. In contrast to the first embodiment of the present invention, the housing of the second embodiment is not rectangular in shape but rather a "tear drop" shape. This tear drop shape may be advantageous in further reducing the overall size of the dispenser or increasing the resistance to applied bending forces, by reducing the length across one side of the dispenser. This embodiment may be especially advantageous where the dispenser is attached to a key ring for example. The ergonomics or aesthetic appeal of the tear drop shape may also be preferable.

Each half of housing 32 is provided with a circular cut-out 33 for engagement with reel 34. An indented or recessed dispensing area 35 is provided in housing 32. Such that the dispensing area 35 lies within the general boundary of the tear drop shape dispenser. Within the recess of the dispensing area 35, a cutter 36 is provided which is adapted to receive and cut dental floss emerging from dispensing aperture 37.

A cover 38 is pivotably moveable with respect to the housing 32. In a first operating condition cover 38 is positioned such that it substantially encloses the dispensing area 35. The cover 38 is also preferably adapted to snugly fit within the recessed portion 39 of the dispensing area 35. The recessed portion 39 provides an overlapping fit between cover 38 and housing 32. The overlapping fit helps to prevent entry of unwanted debris into the dispensing area 35 when the cover is in its first (closed) operating position. The cover 38 is preferably shaped to fit substantially within recess 39 when in its closed (first) operating position.

When pivoted outwards, the cover 38 takes up its second operating position (open) which is shown in FIG. 6. In its open operating position, the dispensing area 35 is exposed in order to allow access to the cutter 36 and the dispensing aperture 37 from which the dental floss exits the housing. When the dispenser is not in use, it is preferable that cover 38 remains in its closed operating position in order to prevent contamination of the dispensing area with dirt and debris. In order to achieve this, a plurality of interacting bumps and recesses 40 and 41 are provided on the housing and cover respectively. In use these interacting bumps and recesses function to index the cover in its closed position so that inadvertent opening of the cover to expose the dispensing area is limited. It is envisioned that similar features may also be provided to index the cover it its fully open position, especially if the cover is biased into its closed position as previously described in relation to the first embodiment.

The housing 32 may also be provided with an aperture 42 which is suitable for use as an attachment means to a key ring or the like. The aperture 42 is preferably configured such that the co-operating halves of the housing 32 form the aperture 42 through the housing without exposing the inner cavity containing reel 34 to the outside environment. This may be achieved by providing an inward protruding flange 51 on one or both halves of the housing, around the aperture 42 such that the aperture is sealed from the environment when the respective halves of the housing 32 are closed. In an analogous manner to that described in the first preferred embodiment of the present invention, the respective housing halves are held together in a substantially sealed manner via a plurality of fastening means 43 and 44. Male fastening means 43 are provided on one respective half of the housing 32 and corresponding female fastening means 44 are provided in complementary positions on the other respective half of housing 32. In use the housing is assembled and snapped closed such that the male protrusions 43 engage tightly with the female fastening means 44.

In a similar manner to the first preferred embodiment, a cutter 36 is fastened to the housing 32 in the dispensing area 35. A guide 45 may also be provided adjacent to dispensing aperture 37, adapted to receive the dental floss after it is unwound from the reel 34 and guide it as it is withdrawn from the housing. The inner surfaces of the guide 45 may be provided with a plurality of barbs which in use act to prevent withdrawal of the dental floss into the housing.

Figure 8:
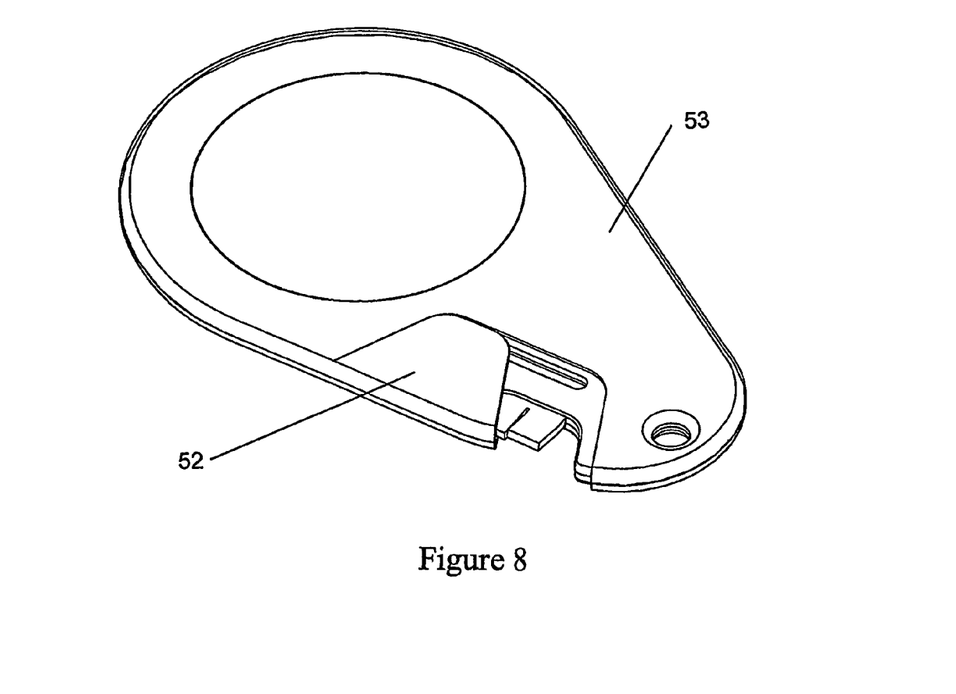
FIG. 8 is a perspective view of a third embodiment of the present invention having a sliding cover.
Figure 9:
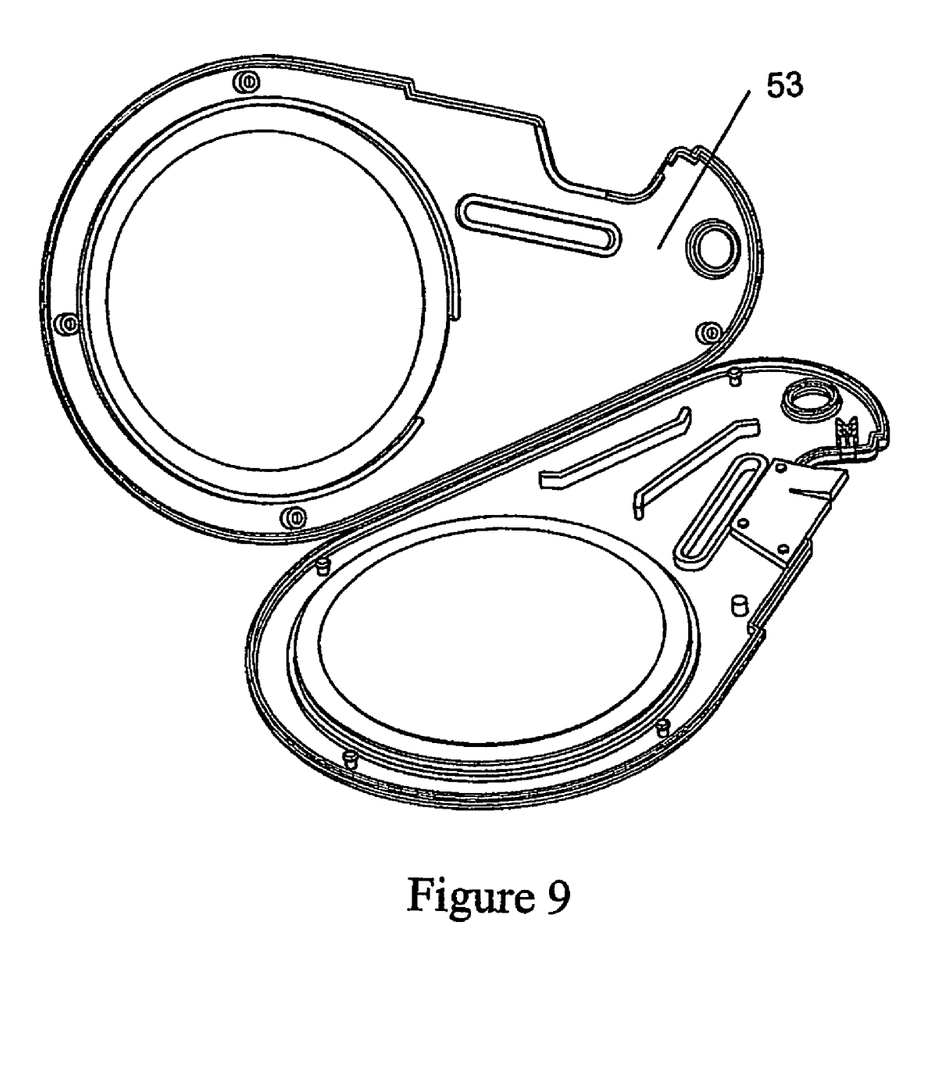
FIG. 9 is an inside view of the dental floss dispenser housing pictured in FIG. 8.

With reference to FIG. 8 and FIG. 9 a third embodiment is pictured to illustrate further options for the present invention. The housing 53 is "tear drop" shaped and the cover 52 is a sliding cover substantially as described in the first embodiment of the present invention. It is also envisaged that a pivoting cover such is that described in the second embodiment of the present invention may also be applied to the rectangular shaped embodiment pictured in FIG. 1.

Likewise where the first embodiment of the present invention illustrated a sliding cover located along the short edge of the rectangular housing, it is anticipated that the sliding cover and dispensing area might be situated along a long edge of a rectangular dispenser in a similar manner to the embodiment shown in FIG. 8.

With reference to FIGS. 10 to 15, a fourth embodiment of the present invention will be described in detail illustrating further options or features or improvements which can be applied to a credit card type dispenser according to the present invention. The fourth embodiment of the present invention comprises a tear drop shape dispenser housing having two substantially planar wall portions 54 which are oppositely disposed one another and narrowly spaced. Each half of the housing has a cut-out aperture 67 for receiving a portion of a floss storage reel.

Figure 10:
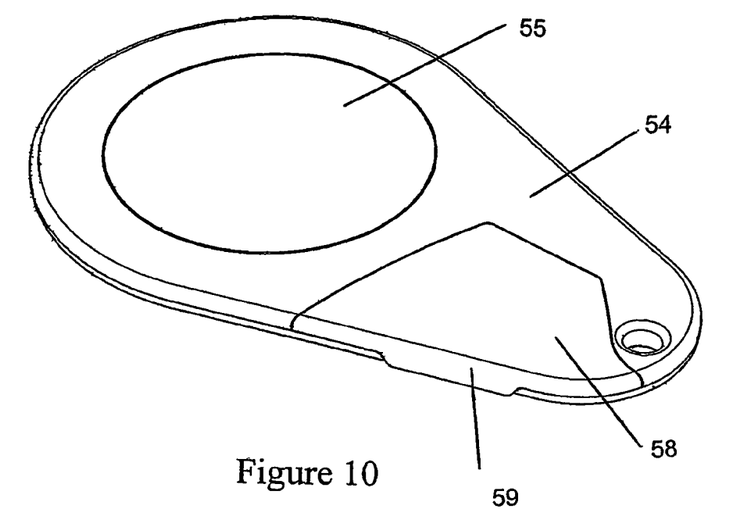
FIG. 10 is a perspective view of a further embodiment of the present invention having a hinged cover shown in its closed position.
Figure 12:
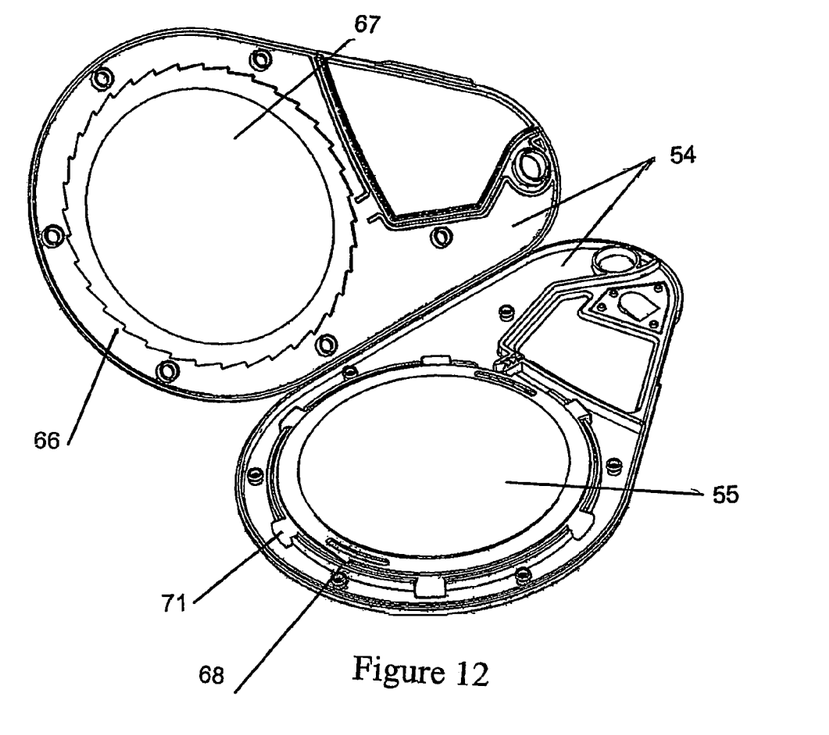
FIG. 12 is an inside view of the dental floss dispenser shown in FIG. 10.
Figure 13:
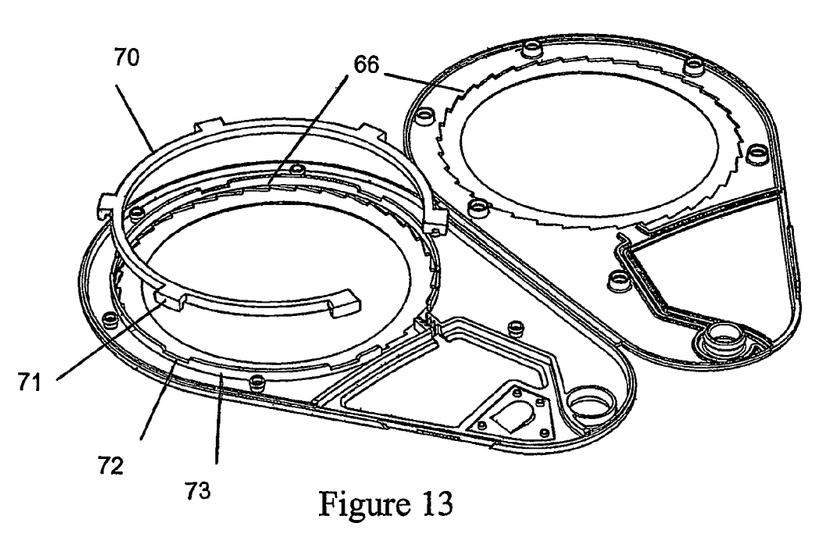
FIG. 13 is a partially exploded view of the dental floss dispenser pictured in FIG. 12.

Reel 55 is situated substantially within a cavity formed between planar wall portions 54. Reel 55 is rotatably mounted between the planar wall portions 54 when the dispenser is assembled so that the reel is able to rotate in order to unwind dental floss as the floss is withdrawn from the dispenser for use. The dental floss dispenser housing 57 comprising two co-operating halves includes (when assembled) a dispensing area 56 toward the narrow end of the tear drop shape. The dispensing area 56 is located adjacent an edge of the housing and is recessed into the housing so that it lies within the outer general tear shaped boundary of the dispenser. A lid or cover 58 is hingedly attached to the upper wall of the housing such that it is moveable between a first (closed) operating condition and a second (open) operating condition. The hinged connection is a living hinge 74. In the first operating condition, cover 58 engages with the planar wall portions and encloses the dispensing area to provide increased hygiene. The cover 58 is movable into a second operating condition wherein the dispensing area and its associated features are accessible to a users fingers for the purpose of withdrawing and cutting a length of dental floss. The cover 58 is provided with a gripping protrusion 59 to allow a users fingers to easily open the cover from the closed position.

Figure 11:
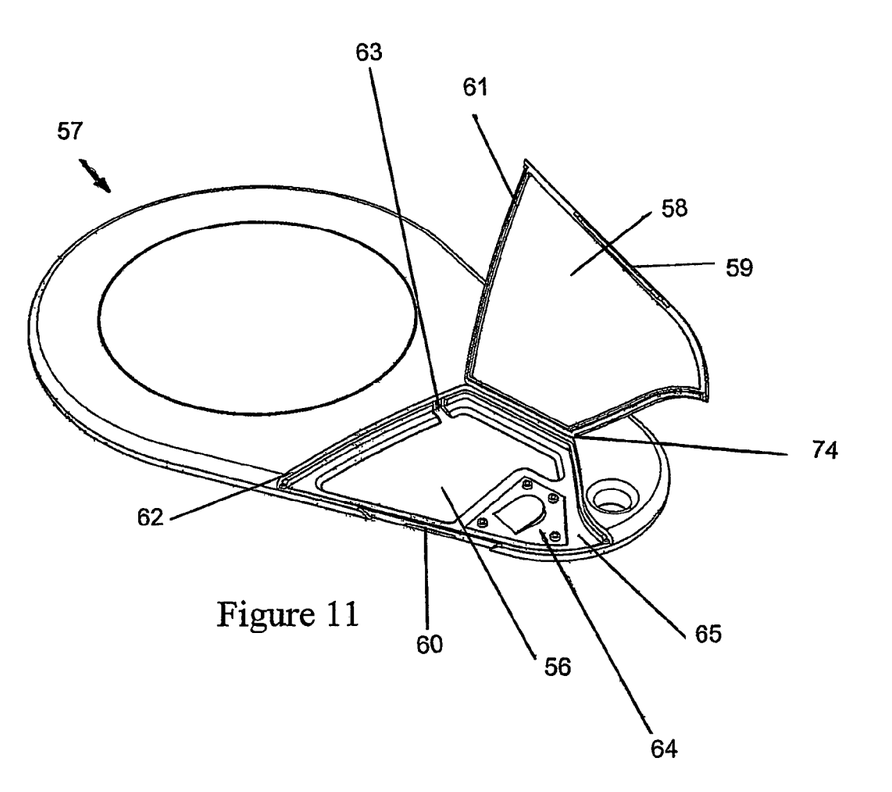
FIG. 11 is a perspective view of the dispenser of FIG. 10 shown with the hinged cover open.

With reference to FIG. 11, the lip portion 59 of cover 58 includes a snap lock type protrusion for mating with a correspondingly shaped snap lock recess 60 located on the opposite wall portion of the dispenser housing 57. Flexing of the cover 58, enables movement between engaged and disengaged positions. Cover 58 may also include a protruding portion 61 around its periphery which is adapted to engage with correspondingly shaped recesses 62. The interaction between protruding rim 61 and corresponding recesses 62 provides an overlapping fit between the cover and the housing around the perimeter of the dispensing area 56, in order to prevent unwanted debris from contaminating the dispensing area when the cover is closed.

Dispensing area 56 also includes dispensing aperture 63 for allowing the dental floss to pass from the portion of the dispenser containing the reel 55 to the dispensing area. Dispensing area 56 also includes cutter 64. Dental floss emerging from dispensing aperture 63, passes through dispensing area 56, to the cutter 64. It is preferable that there is a clear line of sight between dispensing aperture 63 and the open wedge part of the cutter 64. For this purpose the dispensing area 56 includes a mouth portion 65 to allow the dental floss to extend in a straight line well beyond the cutter while not passing too close to the sharp edges of the cutter. The dispensing area 56 is also recessed slightly into the planar wall portion in order to help the users finger to grip the dental floss emerging from dispensing aperture 63.

Figure 14:
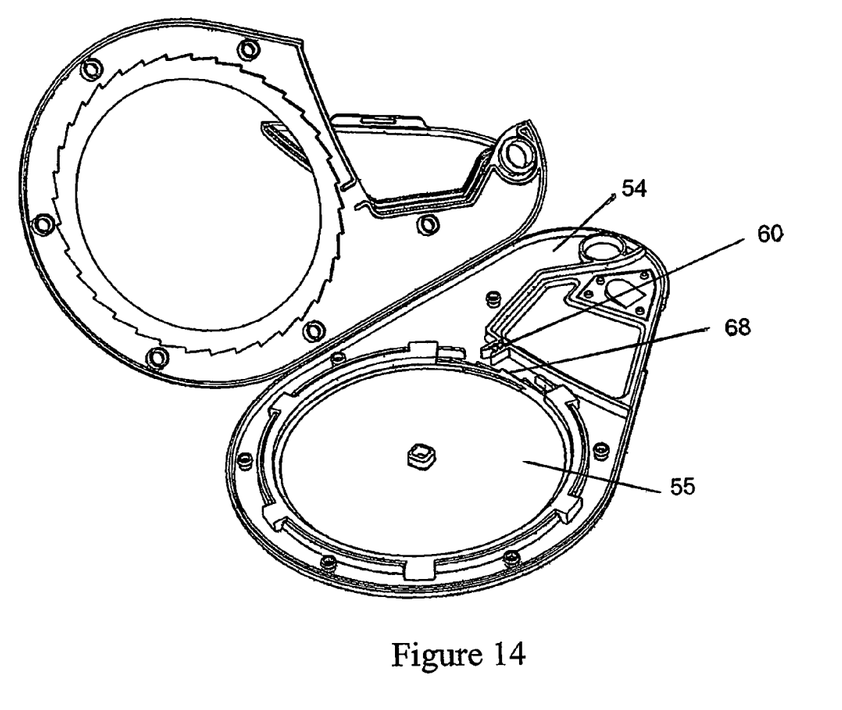
FIG. 14 is a partial sectional view of the dental floss dispenser pictured in FIG. 12.
Figure 15:
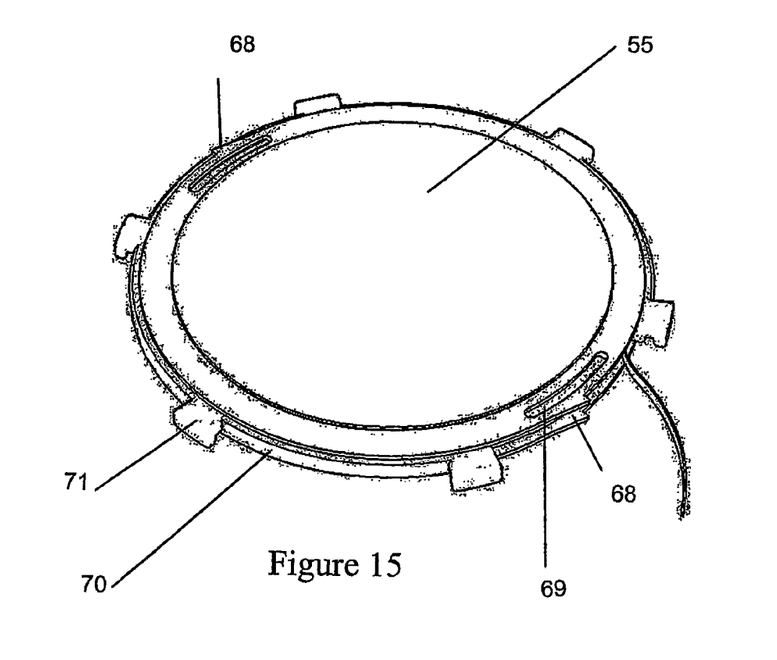
FIG. 15 is a close up view of the floss reel shown in FIG. 12.

It is envisaged that a one-way rotation limiting mechanism may be provided in the dispenser of the present invention in order to prevent the reel 55 from winding the dental floss up so far, that the end of the floss is retracted through the dispensing aperture 63 making it no longer accessible from the dispensing area 56. For this purpose a ratchet mechanism is provided. Ratchet tracks 66 having a series of teeth are located in a circle about the cut-out aperture 67. The outer circumference of the side walls of the reel 55 have flexible ratchet teeth 68 (or pawls) adapted to engage with complementary shaped ratchet tracks 66. The ratchet teeth 68 and tracks 66 are shaped with ramped leading surfaces alternating with radial or under-cut trailing step surfaces. Apertures 69 are provided in the side walls of reel 55 adjacent the ratchet teeth 68 in order to allow the teeth to move by flexing inwards towards the centre of the reel. In use when the dispenser assembly is fully assembled, rotation of the reel 55 in an unwinding direction is possible due to the ramp portions of the ratchet teeth 68, flexing, and sliding up the ramp portions of the correspondingly serrated ratchet tracks 66. As the reel 55 is rotated in an opposite, wind-up, direction, the step portions of ratchet teeth 68 mesh with the corresponding step portions of ratchet tracks 66, preventing rotation of the reel 55 within the dispenser housing. FIG. 14 shows a section reel 55 (showing only one side wall) located within one half of the housing wall 54. In this view, ratchet teeth 68 are shown engaged with correspondingly shaped ratchet track 66.

An incomplete ring shaped spacing member 70 is provided to fit around the periphery of reel 55, between the side walls of the reel. The gap in the ring 70, is aligned with a gap in the floss shielding wall 73, to allow floss to pass from the reel to the dispensing area. The spacing member 70 is narrow so that it does not take up an unnecessary amount of space on the reel which could be used for storing dental floss. The thickness of spacing member 70 is substantially the same as the gap between the side walls of reel 55, in order to prevent the side walls of the reel compressing inwards at their periphery, which may result in the ratchet teeth 68 becoming disengaged from the ratchet tracks 66. In order to prevent the spacing member 70 from rotating with the reel 55 as its unwinds, indexing protrusions 71 are provided outward of the spacer member and are adapted to engage with indexing recesses 72 located in the floss shielding wall 73. In use, the spacer member 70 does not rotate with the unwinding reel 55 and serves to maintain the ratchet teeth 68 in a mating relationship with ratchet tracks 66. The co-operation of the flexible ratchet teeth 68 and ratchet tracks 66 allows the dental floss to be unwound from the reel 55 and pulled from the dental floss dispenser while preventing retraction of the dental floss into the housing by preventing the reel from being wound up in the opposite direction.

The following describes a number of options or variations which maybe applied to a dental floss dispenser of the present invention, as previously described in the embodiments.

Both sliding and pivoting covers may be provided with a plurality of grip improving features such as raised bumps 25 in order to aid the user to grip the cover when opening and closing it, as shown in FIG. 1, and FIG. 6.

The housing or wall portions, reel and the cover are preferably fabricated from a non-metallic material such as plastic in order to improve the ease of production and reduce costs. It is also envisaged that the housing of the dispenser may be constructed from a translucent transparent or opaque material as desired. A translucent or transparent housing may contribute to an increased aesthetic appeal and/or increase the novelty value of the item. Similarly the cover and/or floss reel may also be manufactured from a translucent, transparent or opaque material. An advantage of constructing the reel from a translucent or transparent material arises from the user being able to visually confirm how much dental floss is left on the reel. In the case of a translucent or transparent floss reel, a graphic indicator may be included in order to relate the amount of dental floss remaining to an approximate number of "average floss uses". Alternatively, it may be advantageous to have a metallic cover while the majority of the rest of the parts are plastic.

Preferably the cutter is manufactured from metal in order to provide improved cutting performance.

It is envisaged that a number of methods may be suitable for fastening the housing halves together. The fastening means may be permanent or reversible. A reversible fastening means gives rise to the advantage that the housing may be reopened for the purpose of replacing the dental floss reel. Suitable permanent and non-permanent fastening means for this purpose are envisaged such as gluing, plastic welding, screws or snap lock type fasteners. It is also envisaged that the housing may be manufactured from two distinct pieces and subsequently fastened together, rather than joined by a living hinge, or other appropriate hinge means.

It is envisaged that an alternative method of rotatably mounting the reel within the housing might be suitable if one or both of the housing halves does not include a cut-out. The cut-out may be substituted with a recess of substantially the same shape, but which does not form an aperture all the way through the housing. The raised lip of the floss reel 9 in this case would interact with the recess in substantially the same manner as if the recess were a cut-out. Another alternative method would be to rotatably mount the reel on a shaft or protrusion in a manner commonly appreciated by those skilled in the art.

Alternatively the supply of dental floss may not be wound on to a reel but rather arranged in a coil or a flattened helix. The covering of the dispensing area while also improving the hygiene characteristics of the dispenser also prevents the cutter from damage or causing damage when not in use.

The cut-out in the housing may also be replaced by a transparent window, which would allow inspection of the inner housing and provide improved hygiene.

The dispenser of the present invention is inherently suitable for applications where a compact, easy to use, or an aesthetically pleasing dispenser is required. The dispenser of the present invention is especially suited where increased hygiene is preferred.

The invention claimed is:

1. A dispenser comprising:
    a substantially closed housing having a pair of oppositely disposed substantially planar wall portions, substantially parallel and spaced apart by less than 6 mm, and a dispensing area,
    a supply of dental floss material within said housing, said supply being a reel, said reel including a lip projecting outwardly from a sidewall to define a bearing surface, and
    at least one of said wall portions including a circular aperture therethrough, said circular aperture defining a complimentary bearing surface in said at least one wall portion,
    said circular aperture receiving said lip of said reel such that said reel is rotatably supported between said wall portions with said lip of said reel projecting into said aperture so that said bearing surface of said lip abuts with the complementary bearing surface of said at least one wall portion.

2. The dispenser as claimed in claim 1 wherein said dispenser further comprises:
    a moveable cover connected with said housing to be moveable between a first operating condition, and a second operating condition, wherein said cover when in said first operating condition encloses said dispensing area, and said cover when in said second operating condition exposes said dispensing area.

3. The dispenser as claimed in claim 2, wherein said housing includes a dispensing aperture, opening into said dispensing area and within said dispensing area, and
    a cutter for severing said dental floss material exiting said housing through said aperture.

4. The dispenser as claimed in claim 3, wherein said housing has a general shape defined by a boundary and said dispensing area is recessed into said housing to lie wholly within said boundary of said general shape.

5. The dispenser as claimed in claim 4, wherein said cover in said first operating condition, lies substantially within said boundary.

6. The dispenser as claimed in claim 5, wherein said cover is slidable between said first operating condition and said second operating condition in a sliding direction, and said sliding direction is substantially parallel to said wall portions.

7. The dispenser as claimed in claim 6, wherein said cover is biased toward its said first operating condition.

8. The dispenser as claimed in claim 5, wherein said cover is pivotally moveable between said first and said second operating conditions, and
    the axis of said pivotal motion is substantially perpendicular to said wall portions.

9. The dispenser as claimed in claim 8, wherein said cover is hinged to a said wall portion, and said cover hinging about an axis parallel to said wall portion.

10. The dispenser as claimed in claim 1, wherein said reel includes indicia on an outer surface, and said outer surface is visible through said circular aperture.

11. The dispenser as claimed in claim 2, further comprising:
    a rotation limiting means for preventing rotation of said reel in a wind-up direction,
    said limiting means comprising a ratchet track having a series of teeth with ramped leading surfaces alternating with radial or undercut trailing surfaces on one of said reel or said wall, and at least one complimentary shaped ratchet tooth on the other of said reel or said wall,
    one of said ratchet tooth, or said track teeth being movable,
    said track teeth and said at least one ratchet tooth arranged in a meshing relationship and allowing rotation of said reel in an unwinding direction, by movement of one of said movable ratchet tooth or said movable track teeth, to ride over said other of said ratchet tooth or said track teeth.

12. The dispenser as claimed in claim 11, further comprising an incomplete ring spacer member located between spaced side walls of said reel,
    said ring having a diameter approximately the same as said reel, and said ring having a thickness approximately the same as said space between said side walls,
    said ring including indexing means, and at least one of said walls including correspondingly shaped indexing means,
    said indexing means engaging to prevent rotation of said ring, wherein said filamentary material passes through a gap in said incomplete ring.

13. The dispenser as claimed in claim 2, wherein said wall portions include step portions adapted to lap one another and substantially seal around a perimeter of said wall portions.

14. The dispenser as claimed in claim 2, wherein said wall portions are connected together by a living hinge.

15. The dispenser as claimed in claim 2, wherein said at least one of said wall portions includes a further aperture adapted to receive an attachment means.

16. The dispenser as claimed in claim 2, wherein said cover includes one or more surface features to improve grip.

17. The dispenser as claimed in claim 2, wherein said housing includes at least one guide to direct said dental floss material from said supply to said dispensing area, and
said guide including a plurality of barbs to impede travel of filamentary material through said guide in one direction.

18. The dispenser as claimed in claim 2, wherein said wall portions are fastened together by a reversible fastening means for example, cooperating snap lock fasteners.

19. The dispenser as claimed in claim 2, wherein said reel includes indicia on an outer surface, and said outer surface is visible through said circular aperture.

20. The dispenser as claimed in claim 1 wherein said wall portions are connected together by a living hinge.

21. A dispenser comprising:
a substantially closed housing having a pair of oppositely disposed substantially planar wall portions, substantially parallel and spaced apart by less than 6 mm, and a dispensing area,
a supply of filamentary material within said housing,
said supply being a reel, and
at least one of said wall portions including a circular aperture,
said circular aperture receiving a bearing portion of said reel such that said reel is rotatably supported between said wall portions with said bearing portions projecting into said aperture,
a movable cover connected with said housing to be moveable between a first operating condition, and a second operating condition, wherein said cover when in said first operating condition encloses said dispensing area, and said cover when in said second operating condition exposes said dispensing area,
a rotation limiting means for preventing rotation of said reel in a wind-up direction, said limiting means including a ratchet track having a series of teeth with ramped leading surfaces alternating with radial or undercut trailing surfaces on one of said reel or said wall, and at least one complimentary shaped ratchet tooth on the other of said reel or said wall,
one of said ratchet tooth, or said track teeth being movable, said track teeth and said at least one ratchet tooth being arranged in a meshing relationship and allowing rotation of said reel in an unwinding direction, by movement of one of said movable ratchet tooth or said movable track teeth, to ride over said other of said ratchet tooth or said track teeth,
an incomplete ring spacer member located between spaced side walls of said reel, said ring having a diameter approximately the same as said reel, and said ring having a thickness approximately the same as said space between said side walls,
said ring including indexing means, and at least one of said walls including correspondingly shaped indexing means, said indexing means engaging to prevent rotation of said ring, wherein said filamentary material passes through a gap in said incomplete ring.

* * * * *